United States Patent [19]

Braish

[11] Patent Number: 5,256,791
[45] Date of Patent: Oct. 26, 1993

[54] PREPARATION OF INTERMEDIATES IN THE SYNTHESIS OF QUINOLINE ANTIBIOTICS

[75] Inventor: Tamim F. Braish, Ledyard, Conn.

[73] Assignee: Pfizer Inc., New York, N.Y.

[21] Appl. No.: 844,367

[22] Filed: Mar. 2, 1992

[51] Int. Cl.$^5$ .................. C07D 209/02; C07D 209/52
[52] U.S. Cl. ..................................... 548/452; 548/545
[58] Field of Search ........................... 548/452

[56] References Cited

FOREIGN PATENT DOCUMENTS 64-56673  3/1989  Japan.
102526    3/1991  PCT Int'l Appl..

Primary Examiner—David B. Springer
Attorney, Agent, or Firm—Peter C. Richardson; Paul H. Ginsburg; Karen DeBenedictis

[57] ABSTRACT

This invention relates to novel processes for preparing compounds of the formulae

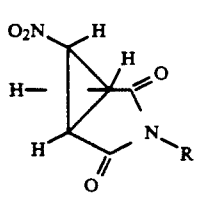 and 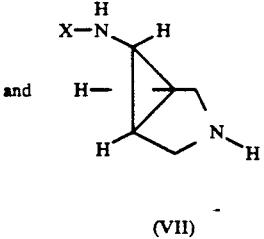

(III)    (VII)

wherein R and X defined as below. Compounds of the formulae VII are useful as intermediates in the syntheses of azabicyclo quinoline carboxylic acids having antibacterial activity. This invention also relates to certain novel intermediates in the syntheses such antibiotics.

18 Claims, No Drawings

PREPARATION OF INTERMEDIATES IN THE SYNTHESIS OF QUINOLINE ANTIBIOTICS

BACKGROUND OF THE INVENTION

This invention relates to novel processes for the preparation of intermediates in the synthesis of the quinoline antibiotic 7-(1α,5α,6α)-(6-amino-3-azabicyclo[3.1.0-]hex-3-yl)-1-(2,4-difluorophenyl)-6-fluoro-1,4-dihydro-4-oxo-1,8-naphthyridine-3-carboxylic acid and related antibiotic compounds. The quinoline antibiotic 7-(1α,5α,6α)-(6-amino-3-azabicyclo[3.1.0]hex-3-yl)-1-(2,4-difluorophenyl)-6-fluoro-1,4-dihydro-4-oxo-1,8-naphthyridine-3-carboxylic acid has the chemical formula

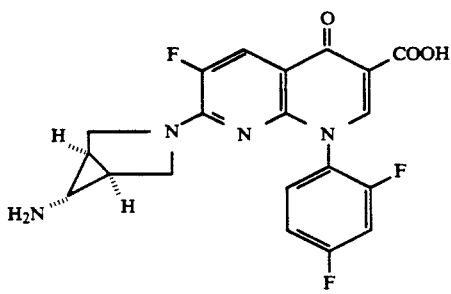

(I)

This compound and related azabicyclo quinoline carboxylic acids that exhibit antibacterial activity are referred to in U.S. patent application Ser. No. 07/551,212, filed on Jul. 11, 1990 and World Patent Application WO 91/02526, filed on Aug. 16, 1989 and published on Mar. 7, 1991. Both of the foregoing applications are assigned in common with the present application and are incorporated herein by reference in their entirety.

The novel methods of this invention may be used to prepare compounds of the formula

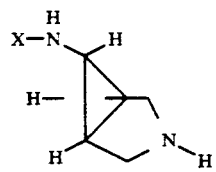

(VII)

which are intermediates in the synthesis of the quinoline antibiotic of the formula I and the azabicyclo quinoline carboxylic acid antibiotics referred to above. The methods by which compounds of the formula VII may be converted into such antibiotic compounds are set forth in detail in U.S. patent application Ser. No. 07/551,212 and World Patent Application WO 91/02526.

SUMMARY OF THE INVENTION

The present invention relates to a process for preparing a compound of the formula

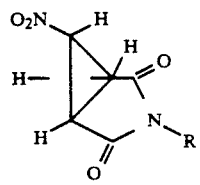

(III)

wherein R is (C₁–C₆) alkyl, (C₃–C₆)cycloalkyl or benzyl, wherein the phenyl moiety of said benzyl group may be substituted, optionally, with one or more substituents independently selected from halo (e.g., chloro, fluoro, bromo or iodo), nitro, (C₁–C₆) alkyl, (C₁–C₆) alkoxy, amino and trifluoromethyl, comprising reacting a compound of the formula

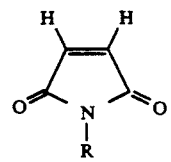

(II)

wherein R is defined as above, with a halonitromethane in the presence of a base.

In a preferred embodiment of this invention, the compound of formula III formed in the above process is a compound wherein R is (C₁–C₆)alkyl or benzyl. In a more preferred embodiment, R is benzyl.

The term "halo", as used herein, refers to chloro, fluoro, bromo or iodo.

This invention also relates to the process described above, further comprising reacting the compound of formula III so formed with a reducing agent to form a compound of the formula

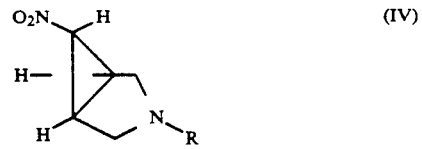

(IV)

wherein R is defined as above.

This invention also relates to compounds having the formula

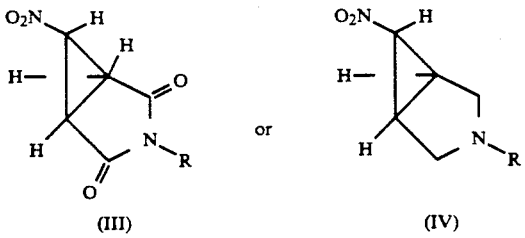

(III)          (IV)

wherein R is defined as above.

DETAILED DESCRIPTION OF THE INVENTION

The processes of the present invention and the preparation of the compounds of the present invention are illustrated in the following reaction scheme. Except where otherwise indicated, in the reaction scheme and discussion that follow, formulas I, II, III and IV, and substituents R and X are defined as above.

SCHEME

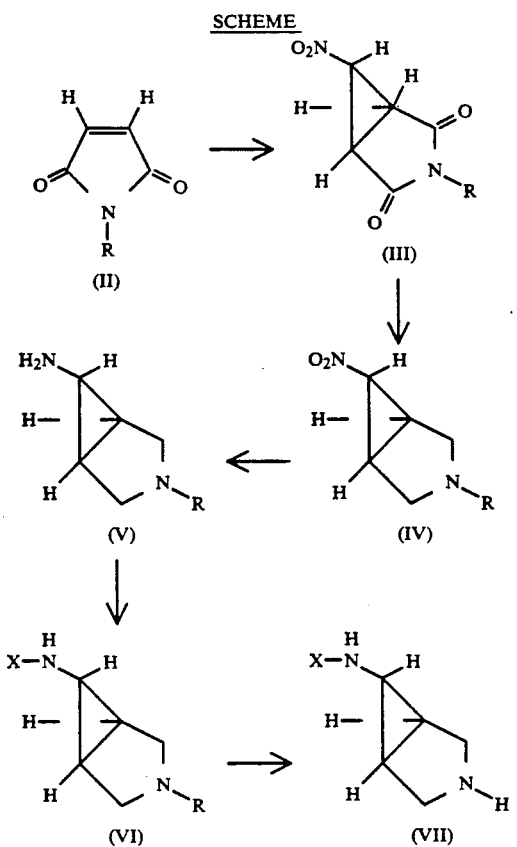

The above reaction scheme illustrates the preparation of compounds of the formula VII, which are useful intermediates in the synthesis of the quinoline antibiotics referred to above.

Referring to the above scheme, reaction of a compound having formula II with a halonitromethane, preferably chloronitromethane ($ClCH_2NO_2$) or bromonitromethane ($BrCH_2NO_2$), in the presence of a base yields the corresponding compound of the formula III. This reaction is generally conducted in an inert, polar, aprotic solvent such as dimethylformamide (DMF), dimethylsulfoxide (DMSO) or dimethylacetamide (DMAC), an inert ethereal solvent such as ethyl ether, glyme or tetrahydrofuran (THF), or another inert solvent such as benzene, toluene or a chlorinated benzene or toluene. Toluene is preferred. Suitable reaction temperatures range from about −78° C. to about 80° C., with about 0° C. being preferred. It is preferable to add the base last. Examples of appropriate bases include carbonate bases such as potassium or sodium carbonate, phosphorine amide bases such as 2-tert-butylimino-2-diethylamino-1,3-dimethylperhydro-1,3,2-diaza-phosphorine, and amine bases such as triethylamine, quanidine, diisopropylethylamine, tetramethylquanidine, 1,8-diazobicyclo-[5.4.0]undec-7-ene (DBU) and 1,5-diazobicyclo-[4.3.0]non-5-ene (DBN). It is advantageous to use an amine base and, most preferably, to use DBU.

Reduction of the compound of formula III so formed yields the corresponding compound of formula IV. Appropriate reducing agents include borane/dimethylsulfide, borane/THF, sodium borohydride and a borontrifluoride.etherate mixture. The preferred reducing agent is borane/THF. The reduction is typically carried out at temperatures ranging from about 45° C. to about 90° C., in an inert ethereal solvent such as glyme, diglyme, diethylether, diisopropyl ether or THF. It is preferably carried out at about 66° C. in THF.

The resulting compound of the formula IV may be converted into the corresponding amine of formula V by treating it with a metal and an inorganic acid. The preferred metal is zinc. Suitable inorganic acids include hydrochloric acid, sulfuric acid. Hydrochloric acid is preferred. This reaction is generally conducted in a lower alcohol solvent such as ethanol, methanol, 1-propanol or 2-propanol, preferably ethanol, at a temperature from about 0° C. to about 80° C., preferably at about 25° C.

The corresponding compound of formula VI, wherein X is a nitrogen protecting group, is then formed by adding a suitable nitrogen protecting group to the unsubstituted amino nitrogen of the compound of formula V. Several well known nitrogen protecting groups can be used. Such groups include ($C_2-C_6$) alkoxycarbonyl, optionally substituted benzyloxycarbonyl, aryloxycarbonyl, silyl, trityl, vinyloxycarbonyl, O-nitrophenylsulfonyl, diphenylphosphinyl, p-toluenesulfonyl, and benzyl. It is advantageous to use di-t-butyldicarbonate or 2-t-butoxycarbonyloxyimino-2-phenylacetonitrile. The addition of the nitrogen protecting group is usually carried out in a chlorinated hydrocarbon solvent such as methylene chloride or 1,2-dichloroethane, or an ethereal solvent such as glyme, diglyme or THF, in the presence or absence of a catalytic amount of an amine base such as triethylamine, diisopropylethylamine or pyridine, preferably triethylamine, at a temperature from about 0° C. to about 50° C., preferably at about 25° C.

When R is benzyl, the hydrogenolytic removal of the R group from the compound of formula VI formed in the foregoing step yields the desired compound of formula VII. This is generally accomplished by reacting the compound of formula VI, wherein R is benzyl, with hydrogen gas at a pressure from about 0 psi to about 2000 psi, preferably about 50 psi, in the presence of a noble catalyst such as palladium, platinum or rhodium. Palladium on carbon or palladium hydroxide on carbon is preferred. The temperature may range from about 20° C. to about 80° C., and is preferably about 25° C. The solvent is usually a lower alcohol and is preferably methanol.

When R is ($C_1-C_6$) alkyl or ($C_3-C_6$) cycloalkyl, the R group may be removed by reaction with α-chloroethylchloroformate (ACE-Cl). (See Olefson et al., *J. Org. Chem.*, 49, 2081-2 (1984) and Olefson et al., *Pure & Appl. Chem.*, 60(11), 1715-24 (1988)).

The procedures by which compounds of the formula VII may be used to prepare the quinoline antibiotic having formula I and related azabicyclo quinoline carboxylic acid antibiotics are set forth in U.S. patent application Ser. No. 07/551,212, filed on Jul. 11, 1990 and World Patent Application, WO 91/02526, filed on Aug. 16, 1989 and published on Mar. 7, 1991, both of which are incorporated herein by reference in their entirety.

The antibacterial compound having formula I and the related azabicyclo quinoline carboxylic acid antibiotics that can be synthesized using the methods and compounds of this invention are useful in the treatment of animals, including humans, having bacterial infections. They are useful in treating bacterial infections of broad spectrum, particularly in treating gram-positive bacterial strains.

U.S. patent application Ser. No. 07/551,212 and World Patent Application WO 91/02526 set forth in detail the appropriate dosage ranges and methods of administration of such antibiotic compounds. These references also set forth a method by which the antibacterial activity of such compounds may be determined.

The following examples illustrate the methods and compounds of the present invention. It will be understood, however, that the invention is not limited to the specific details of these examples.

EXAMPLE 1

1α, 5α, 6α-3-Benzyl-6-nitro-2,4-dioxo-3-azabicyclo[3.1.0]hexane

To N-benzylmaleimide (24.3 g, 130 mmol) and bromonitromethane (18.2 ml, 260 mmol) was added 250 ml of toluene and the mixture was cooled to 0° C. while stirring vigorously with an overhead stirrer, 1,8-diazabicyclo[5.4.0]undec-7-ene (DBU) (58 ml, 390 mmol) diluted with 200 ml of toluene was added dropwise over a period of 30 min. The reaction was allowed to stir for 2 additional hours at room temperature. The toluene layer was decanted and washed with (2×100 ml) 0.1M HCl solution and dried over magnesium sulfate ($MgSO_4$). Evaporation of the solvent provided 5.4 g of the product which represents a 17% yield. M.P.=114°-115.5° C. $^1$H NMR ($CDCl_3$): 7.31 (m, 5H, aromatics), 4.54 (s, 2H, benzylic), 4.47 (t, 1H, alpha to nitro), 3.35 (d, 2H, 3-ring).

EXAMPLE 2

1α, 5α, 6α-3-Benzyl-6-nitro-3-azabicycolo[3.1.0]hexane

To the 1α, 5α, 6α-3-benzyl-6-nitro-2,4-dioxo-3-azabicyclo[3.1.0]hexane (2 g, 8.1 mmol) from Example 1 in 20 ml of THF was added borane.THF complex (32.4 ml of 1M solution in THF, 32.4 mmol) and the mixture was heated to reflux for 3 hours. The reaction was cooled to room temperature and 10 ml of methanol was carefully added. Heating to reflux was then resumed for 15 min. The solvent was then evaporated and the residual oil was dissolved in 200 ml of $CH_2Cl_2$ and washed with water (3×100). The organic layer was dried over $MgSO_4$ and evaporated to provide 1.5 g of the product (light oil) which represents a 90% yield. $^1$H NMR ($CDCl_3$): 7.35-7.19 (m, 5H, aromatics), 4.63 (t, 1H, alpha to nitro), 3.59 (s, 2H, benzylic), 3.14 (m, 2H, 5-ring), 2.49 (m, 2H, 5-ring), 2.51 (m, 2H, 3-ring).

EXAMPLE 3

1α, 5α, 6α-3-Benzyl-6-amino-3-azabicyclo[3.1.0]hexane

To the 1α, 5α, 6α-3-benzyl-6-nitro-3-azabicyclo[3.1.0]hexane (6 g, 27.5 mmol) from Example 2 in 50 ml of ethanol was added zinc dust (18.0 g, 275 mmol). To that was added 150 ml of 1M HCl solution at such a rate that the temperature of the reaction never exceeded 40° C. (1 hour). The reaction was allowed to stir at room temperature for 3 hours after which it was filtered through Celite ®. The solvents were then evaporated and the thick white residue was digested with 500 ml of 1M NaOH solution for 3 hours. The mixture was extracted with (2×300 ml) $CH_2Cl_2$ and the combined organic layers were washed with brine (3×100) and dried over $MgSO_4$. Evaporation of the solvent provided 4.06 g of the product which represents a 79% yield. $^1$H NMR ($CDCl_3$): 7.35-7.20 (m, 5H, aromatics), 4.62 (broad singlet, 1H, alpha to nitro), 3.60 (s, 2H, benzylic), 3.14 (m, 2H, 5-ring), 2.52 (m, 2H, 5-ring and m, 2H, cyclopropyl).

EXAMPLE 4

1α, 5α, 6α-3-Benzyl-6-[(t-butyl formyl)amino]-3-azabicyclo[3.1.0]hexane

To the 1α, 5α, 6α-3-benzyl-6-amino-3-azabicyclo[3.1.0]hexane from Example 3 (3.75 g, 19.9 mmol) in 50 ml of THF was added di-t-butyl dicarbonate (4.78 g, 21.9 mmol) and triethylamine (0.28 ml, 1.99 mmol), and the mixture was allowed to stir for 4 hours. The solvent was then evaporated and 75 ml of methylene chloride ($CH_2Cl_2$) was added. The mixture was washed with 20 ml of water and dried over $MgSO_4$. The solvent was evaporated and replaced with 100 ml of hexane. The mixture was heated until all the solids dissolved and 2.5 g of activated charcoal was added and heating was continued for 5 min. The carbon was filtered. Upon cooling the reaction mixture, a solid formed which was filtered and dried in air. The product weighed 5.1 g which represents an 89% yield. M.P.=131°-132° C. (white needles). $^1$H NMR ($CDCl_3$): 7.24 (m, 5H, aromatics), 3.54 (s, 2H, benzylic), 3.06 (m, 2H, 5-ring), 2.91 (broad, 1H, alpha to amide), 2.43 (m, 2H, 5-ring), 1.52 (m, 2H, 3-ring).

EXAMPLE 5

1α, 5α, 6α-[(t-Butyl formyl)amino]-3-azabicyclo[3.1.0]hexane

To 1α, 5α, 6α-3-benzyl-6-[(t-butyl formyl)amino]-3-azabicyclo[3.1.0]hexane from Example 4 (2.0 g, 6.94 mmol) in 50 ml of methanol was added palladium hydroxide on carbon ($Pd(OH)_2$/C) (50% wet) (1.0 g, 50% by weight). The mixture was hydrogenated at 50 PSI for 6 hours and was then filtered through Celite ® and the solvent was evaporated to provide 1.36 g of the product in 99% yield. $^1$H NMR ($CDCl_3$): 3.22-2.95 (m, 4H, 5-ring), 2.61 (broad, 1H, amide), 2.32 (m, 1H, alpha to amide), 1.63 (m, 2H, 3-ring), 1.45 (s, 9H, butyl).

What is claimed is:

1. A process for preparing a compound of the formula

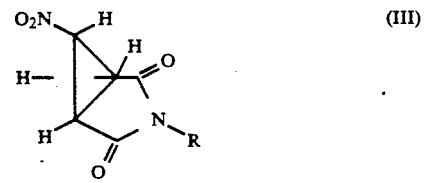

wherein R is ($C_1$-$C_6$) alkyl, ($C_3$-$C_8$) cycloalkyl or benzyl, wherein the phenyl moiety of said benzyl group may be substituted, optionally, with one or more substituents independently selected from halo, nitro, ($C_1$-$C_6$) alkyl, ($C_1$-$C_6$) alkoxy, amino and trifluoromethyl, comprising reacting a compound of the formula

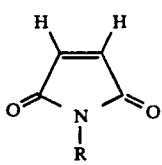
(II)

wherein R is defined as above, with a halonitromethane in the presence of a base.

2. A process according to claim 1, wherein the compound of formula III produced is a compound wherein R is (C₁-C₆)alkyl or benzyl.

3. A process according to claim 2, wherein R is benzyl.

4. A process according to claim 1, wherein said halonitromethane is bromonitromethane or chloronitromethane.

5. A process according to claim 1, wherein said process is carried out at a temperature from about −78° C. to about 80° C.

6. A process according to claim 1, wherein said process is carried out in a solvent selected from benzene, toluene, dimethylformamide or tetrahydrofuran.

7. A process according to claim 6, wherein said solvent to toluene.

8. A process according to claim 1, wherein said base is selected from carbonate bases, amino bases and phosphorine amide bases.

9. A process according to claim 8, wherein said base is selected from the group consisting of sodium carbonate, sodium bicarbonate, potassium carbonate, potassium bicarbonate, 2-tert-butylimino-2-diethylamino-1,3-dimethylperhydro-1,3,2-diazaphosphorine, triethylamine, guanidine, diisopropylethylamine, tetramethylguanidine, 1,8-diazabicyclo[5.4.0]undec-7-ene and 1,5-diazabicyclo[4.3.0]non-5-ene.

10. A process according to claim 9, wherein said base is 1,8-diazabicyclo[5.4.0]undec-7-ene.

11. A process according to claim 1, further comprising reacting the compound of formula III formed in said process with a reducing agent to form a compound of the formula

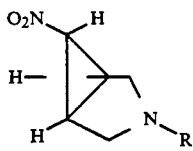
(IV)

wherein R is defined as in claim 1.

12. A process according to claim 11, further comprising reacting the compound of formula IV formed in said process with zinc and an inorganic acid to form the corresponding amine having the formula

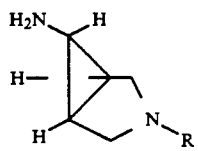
(V)

wherein R is defined as in claim 11.

13. A process according to claim 12, wherein said acid is hydrochloric acid or sulfuric acid.

14. A process according to claim 11, wherein said reducing agent is borane.tetrahydrofuran complex.

15. A process according to claim 12, further comprising adding a nitrogen protecting group to said compound of formula (V) to form a compound of the formula (VI).

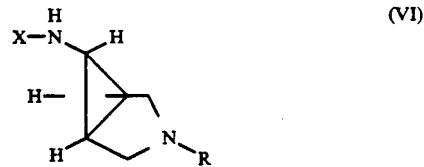
(VI)

wherein R is defined as in claim 12 and X is a nitrogen protecting group.

16. A process according to claim 15, wherein said compound of the formula (V) is reacted with di-t-butyldicarbonate or 2-t-butyoxycarbonyloxymino-2-phenylaceto-nitrite to form a compound of the formula (VI) wherein X is t-butoxycarbonyl.

17. A process according to claim 15, which produces a compound of the formula VI wherein R is benzyl or substituted benzyl, further comprising subjecting said compound of formula VI to hydrogenolytic removal of the R group to form a compound of the formula

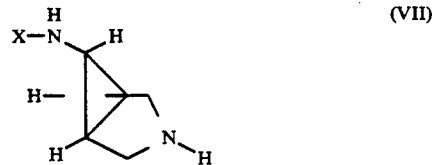
(VII)

wherein X is defined as in claim 15.

18. A process for preparing a compound of the formula

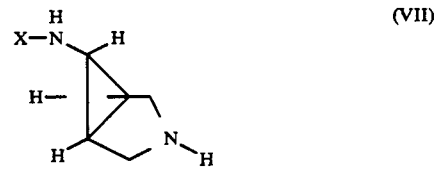
(VII)

wherein X is a nitrogen protecting group, comprising:
(a) reacting a compound of the formula

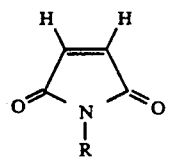
(II)

wherein R is (C₁-C₆)alkyl, (C₃-C₈)cycloalkyl or benzyl, wherein the phenyl moiety of said benzyl group may be substituted, optionally, with one more substituents independently selected from halo, nitro, (C₁-C₆)alkyl, (C₁-C₆)alkoxy, amino and trifluoromethyl, with a halonitromethane in the present of a base to form a compound of the formula

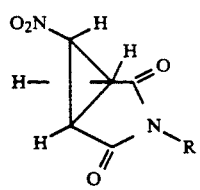

(III)

wherein R is defined as above;
(b) reacting said compound of formula III formed in step "a" with a reducing agent to form a compound of the formula

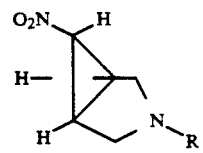

(IV)

wherein R is defined as above;
(c) reacting said compound of formula IV formed in step "b" with zinc and an inorganic acid to form the corresponding amine having the formula

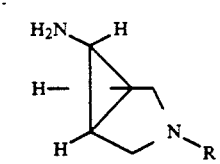

(V)

wherein R is defined as above;
(d) adding a nitrogen protecting group to said compound of formula V formed in step "c", to form a compound of the formula

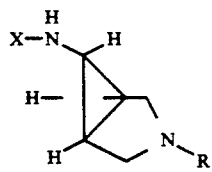

(VI)

wherein R is defined as above and X is a nitrogen protecting group; and
(e) subjecting said compound of the formula VI, if R is benzyl or substituted benzyl, to hydrogenolytic removal of the R group.

* * * * *